United States Patent
Cai et al.

(10) Patent No.: US 9,642,358 B2
(45) Date of Patent: May 9, 2017

(54) ANTIMICROBIAL LIGHTING SYSTEM

(71) Applicant: GE Lighting Solutions LLC, East Cleveland, OH (US)

(72) Inventors: Dengke Cai, Willoughby, OH (US); Matthew A Bugenske, Shaker Heights, OH (US); Sebastien Magnan, Montreal (CA); Francois Turgeon, St-Eustache (CA); Jean-Francois Richard, St-Hubert (CA); Angela Wong, Dorval (CA)

(73) Assignee: GE LIGHTING SOLUTIONS LLC, East Cleveland, OH (US)

( * ) Notice: Subject to any disclaimer, the term of this patent is extended or adjusted under 35 U.S.C. 154(b) by 19 days.

(21) Appl. No.: 14/103,873

(22) Filed: Dec. 12, 2013

(65) Prior Publication Data
US 2015/0164067 A1    Jun. 18, 2015

(51) Int. Cl.
F21V 3/00 (2015.01)
F21V 5/00 (2015.01)
A01N 25/08 (2006.01)
A01N 25/10 (2006.01)
A01N 25/34 (2006.01)

(52) U.S. Cl.
CPC ............ *A01N 25/08* (2013.01); *A01N 25/10* (2013.01); *A01N 25/34* (2013.01)

(58) Field of Classification Search
CPC ........ A01N 25/08; A01N 25/10; A01N 25/34; A01N 31/16; A01N 33/12; A01N 59/16; A01N 59/20; F21S 4/00; F21S 8/00; F21S 8/03; F21S 8/031; F21S 8/04; F21V 3/04; F21V 3/0409; F21V 3/0427; F21V 3/0436; F21V 3/0445; F21V 3/0454; F21V 3/0463; F21V 3/0472; F21V 3/0481
USPC .... 362/249.01, 217.02, 223, 311.01, 311.03, 362/330
See application file for complete search history.

(56) References Cited

U.S. PATENT DOCUMENTS

| 6,764,655 | B1 | 7/2004 | Nishii et al. |
| 7,327,074 | B2 | 2/2008 | Fujishima et al. |
| 7,667,407 | B2 * | 2/2010 | Schlitt et al. ............. 313/635 |

(Continued)

FOREIGN PATENT DOCUMENTS

| EP | 1759034 | 10/2008 |
| EP | 2028417 A1 | 2/2009 |

(Continued)

OTHER PUBLICATIONS

Seery et al., "Silver Doped Titanium Dioxide Nanomaterials for Enhanced Visible Light Photocatalysis", Journal of Photochemistry and Photobiology A: Chemistry, pp. 258-263, 2007.

(Continued)

*Primary Examiner* — Jason Moon Han
(74) *Attorney, Agent, or Firm* — GE Global Patent Operation; Peter T. DiMauro (57) ABSTRACT

Provided is a system enhancing control of bacterial growth by combining antimicrobial additives and surface microstructure patterns on outer surfaces of a device, such as a lighting fixture. The system physically decreases bio-adhesion between microbes and substrates applied to the outer surfaces. The system combines a surface micro-structured component with an antimicrobial component to generate a single component.

17 Claims, 5 Drawing Sheets

(56) References Cited

U.S. PATENT DOCUMENTS

| | | | |
|---|---|---|---|
| 8,080,490 B2* | 12/2011 | Fechner et al. | 501/24 |
| 8,318,282 B2 | 11/2012 | Ylitalo et al. | |
| 8,512,322 B1 | 8/2013 | Liu et al. | |
| 2003/0035750 A1* | 2/2003 | Neuberger | 422/22 |
| 2003/0108716 A1* | 6/2003 | Nun et al. | 428/141 |
| 2003/0134086 A1 | 7/2003 | Nun et al. | |
| 2003/0147932 A1 | 8/2003 | Nun et al. | |
| 2004/0090429 A1* | 5/2004 | Geaghan et al. | 345/173 |
| 2004/0228826 A1* | 11/2004 | Yamamoto et al. | 424/70.122 |
| 2006/0086252 A1 | 4/2006 | Huang | |
| 2006/0210634 A1* | 9/2006 | Moerck et al. | 424/484 |
| 2007/0000407 A1* | 1/2007 | Leong | 106/15.05 |
| 2007/0237945 A1* | 10/2007 | Ohrlander et al. | 428/328 |
| 2009/0041632 A1 | 2/2009 | Day et al. | |
| 2009/0103307 A1* | 4/2009 | Shu | 362/294 |
| 2009/0197494 A1 | 8/2009 | Chang et al. | |
| 2009/0238811 A1 | 9/2009 | McDaniel et al. | |
| 2010/0126404 A1 | 5/2010 | Brennan et al. | |
| 2010/0143964 A1 | 6/2010 | Mor et al. | |
| 2010/0272988 A1 | 10/2010 | Wu et al. | |
| 2010/0279066 A1 | 11/2010 | Bulliard et al. | |
| 2011/0098724 A1 | 4/2011 | Cichocki et al. | |
| 2012/0058302 A1 | 3/2012 | Eggenspieler et al. | |
| 2013/0211310 A1* | 8/2013 | Bommarito | B08B 17/06 602/48 |
| 2013/0273132 A1* | 10/2013 | Eddy | 424/411 |

FOREIGN PATENT DOCUMENTS

| | | |
|---|---|---|
| EP | 2088131 | 8/2009 |
| WO | 2009056838 A1 | 5/2009 |

OTHER PUBLICATIONS

Pucher et al., "Nano-TiO2 Sols Immobilized on Porous Silica as New Efficient Photocatalyst", Applied Catalysis A: General, vol. No. 332, Issue No. 2, pp. 297-303, Nov. 1, 2007.

Giulio et al., "Photo-catalytic Coating of Polystyrene for Household Cooling Appliances with Self Cleaning Surfaces", Journal of Applied Electrochemistry, vol. No. 39, Issue No. 11, pp. 2265-2273, 2009.

Zhou et al., "Ag2O/TiO2 Nanobelts Heterostructure with Enhanced Ultraviolet and Visible Photocatalytic Activity", Applied Materials & Interfaces, vol. No. 2, Issue No. 8, pp. 2385-2392, 2010.

Winzenburg et al., "Efficient Photocatalysis in the Visible with TiO2/Phthalocyanine-Hybrid Particles", 3rd International Symposium on Ultra-High Performance Concrete and Nanotechnology for High Performance Construction Materials, pp. 177-184, 2012.

International Search Report and Written Opinion issued in connection with corresponding PCT Application No. PCT/US2014/065661 on May 12, 2015.

The U.S. Office Action issued in connection with related U.S. Appl. No. 14/081,805 on Sep. 4, 2015.

PCT Search Report and Written Opinion issued in connection with corresponding PCT Application No. PCT/US2014/071148 on Sep. 10, 2015.

US Final Office Action issued in connection with related U.S. Appl. No. 14/081,805 on Apr. 19, 2016.

Matthew A. Bugenske et al., U.S. Appl. No. 14/081,805, filed Nov. 15, 2013.

* cited by examiner

ANTIMICROBIAL LIGHTING SYSTEM

I. FIELD OF THE INVENTION

The present invention relates generally to the field of antimicrobial lighting fixtures. More particularly, the present invention relates to mitigating or controlling bacterial growth in lighting fixture applications at healthcare facilities.

II. BACKGROUND OF THE INVENTION

It is estimated that between 5% and 10% of patients admitted to hospitals acquire one or more healthcare-associated infections, which leads to more than a million people worldwide being affected by infections acquired in hospitals. Health-care associated infections are also an important problem in extended care facilities, including nursing homes and rehabilitations units. These health-care acquired infections are associated with nearly 100,000 deaths annually.

Patients infected with healthcare-associated microbes frequently contaminate items in their immediate vicinity with microbes that may remain viable on surfaces for days to weeks. Contaminated surfaces in healthcare facilities contribute to the spread of healthcare-associated microbes. In some instances, patients acquire microbes following direct contact with contaminated equipment or other surfaces. Contaminated surfaces can act as sources from which healthcare workers contaminate their hands. Healthcare workers can contaminate their hands by touching contaminated surfaces, and can transmit microbes if their hands are not cleansed appropriately.

Inadequate cleaning of rooms after discharging a patient with certain contagious diseases put subsequent patients admitted to the room at risk of acquiring the organism. Routine cleaning of patient rooms is often below the required standard. Therefore, improved cleaning and disinfection of the environment can reduce the risk of patients acquiring multi-drug resistant microbes. Cleaning, disinfecting and sterilization save lives and improve patient outcomes. Providing patients with a safe environment of care requires appropriate cleaning and disinfection of medical equipment and environmental surfaces.

Furthermore, many microbes can form multicellular coatings, called biofilms. Biofilms are any group of microorganisms in which cells stick to each other on a surface. Biofilms can facilitate the proliferation and transmission of microorganisms by providing a stable protective environment. Biofilms can be prevalent in facilities such as hospitals, schools, public restrooms, restaurants, bars, club houses, and daycare centers.

Accordingly, much research has been devoted toward preventing colonization of microbes on the surfaces in such facilities, especially healthcare facilities, and preventing growth of bacteria by the use of antimicrobial agents. Various types of antimicrobials, such as triclosan and silver, have been in use for many years.

The most common antimicrobial being incorporated into materials is silver. Silver is a powerful, natural antibiotic and is one of the oldest antimicrobial agents on record. Silver derives its broad spectrum antimicrobial activity from the ability of silver ions. Silver ions released from the antimicrobial agent, come in contact with microbes and the microbes are inhibited.

With the presence of moisture, the antimicrobial additives release a few silver ions gradually. Silver ions have an ability to strongly bind to the cellular enzyme of microbes and inhibit enzyme activity of the cell wall, membrane, and nucleic acids. As microbes have a negative surface charge, silver ions with a positive charge are drawn toward the microbes, and disturb their electric balance and disrupts their electron transfer. The result is that the microbes burst their cell walls and are extinguished.

Otherwise, silver ions are taken into the microbes where they react and bond to the cellular enzyme microbes. Acting as a catalyst, silver disables the enzyme that one-cell bacteria, viruses and fungi need for their oxygen metabolism. This inhibits enzyme activity and multiplication of the microbes by suffocation, thus resulting in death of the microbes.

Thus, antimicrobial agents have been found to be useful blended with materials such as plastics, paintings and coatings, which also have applications in facilities such as hospitals. In particular, such antimicrobial agents have been adapted for incorporation within plastic, paint, and coating compositions to produce industrial, consumer and household products, which exhibit antimicrobial characteristics.

Although silver is a powerful antimicrobial agent, these coatings of antimicrobial agent are not intended as a substitute for good hygiene. Coated products must still be cleaned to ensure the surfaces will be free of destructive microbes. Commercially available antimicrobial materials usually require regular cleaning every 3-4 days. This is because existing technologies like triclosan or ionic silver technologies require moisture to activate the reactions in order to reduce bacterial grow. After coming in contact with water, an antimicrobial material, for example silver, releases effective amount of silver ions to inhibit the growth of microbes. But more importantly, the build-up of dead microbes on the surfaces of the material prevents new microbes from making contact with the antimicrobial active ingredients. Therefore, the antimicrobial efficacy will decrease over time.

Thus, there remains a need for a system and method that provides lighting devices with effective antimicrobial activity in order to reduce the growth of bacteria, without increasing the antimicrobial levels, which are restricted by U.S. Environmental Protection Agency (EPA) and U.S. Food and Drug Administration (FDA) regulations. The EPA and FDA regulate antimicrobial products to assess the potential dangers and risks to human health and the environment.

Currently, there are more than 5,000 antimicrobial products registered with the EPA and sold in the marketplace. Nearly 60 percent of antimicrobial products are registered to control infectious microorganisms in hospitals and other health care environments.

Because antimicrobials are considered pesticides, regulation of antimicrobial plastic additives in the U.S. is generally the domain of the EPA under the Federal Insecticide, Fungicide and Rodenticide Act (FIFRA). If a product claims to be effective in controlling specific microorganisms (such as, *E. coli*, *S. aureus*, and *Salmonella*), it must be registered as a pesticide because the EPA considers this a public health claim. The EPA regulations do not cover the use of antimicrobials in medications or food additives.

The FDA has broad jurisdiction to regulate the safety and effectiveness of products that constitute foods, dietary supplements, cosmetics, drugs, biological, or medical device products. Where antimicrobial claims in labeling or advertising are made stating that the product is intended for use in the prevention or mitigation of disease in man or animals, such products are subject to FDA regulations.

There are some antimicrobial additives for which the proposed uses are regulated by the FDA as food additives and regulated by the EPA as pesticides. In this case, there are joint regulations where the antimicrobial product may have to comply with the requirements of both the EPA and FDA.

III. SUMMARY OF EMBODIMENTS OF THE INVENTION

Given the aforementioned deficiencies, a need exists for systems and methods and systems that decreases bio-adhesion between microbes and substrates, but also provides optical veiling and diffusing effect to meet lighting distribution requirements. There also remains a need for an environmental cleaning and antimicrobial lighting method and device that reduces the need for frequent cleaning requirements.

In certain embodiments, the system and method enhances the control of bacterial growth by combining antimicrobial additives and surface micro-structure patterns onto outer surfaces of devices, such as a lighting fixture. The combination also physically decreases bio-adhesion between microbes and substrates applied to the outer surfaces of the devices. The system and method combines a surface micro-structured component with an antimicrobial component to generate a single component.

In certain embodiments, the system and method combines antimicrobial additives and a surface micro-structure pattern on outer surfaces on devices, such as a lighting fixture, without using any antimicrobial additives, which are restricted by EPA and FDA regulations. Bio-adhesion between microbes and the substrates of the device is physically decreased by a patterned micro-sized surface and hydrophobic surface.

An antimicrobial additive is blended into an outer component of a device, such as a lighting fixture, configured to be exposed to air in order to provide an antimicrobial blended outer component to control the growth of microbes. The combined techniques of the system and method improve various performance aspects of the lighting fixture, such as killing and inhibiting growth of anti-microbes, reducing bio-adhesion, cleaning the surrounding air, and facilitating ease of cleaning maintenances.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

The present invention may take form in various components and arrangements of components, and in various process operations and arrangements of process operations. The present invention is illustrated in the accompanying drawings, throughout which, like reference numerals may indicate corresponding or similar parts in the various figures. The drawings are only for purposes of illustrating preferred embodiments and are not to be construed as limiting the invention. Given the following enabling description of the drawings, the novel aspects of the present invention should become evident to a person of ordinary skill in the art.

V. DETAILED DESCRIPTION OF VARIOUS EMBODIMENTS

The following detailed description is merely exemplary in nature and is not intended to limit the applications and uses disclosed herein. Further, there is no intention to be bound by any theory presented in the preceding background or summary or the following detailed description.

Throughout the application, description of various embodiments may use "comprising" language, however, it will be understood by one of skill in the art, that in some specific instances, an embodiment can alternatively be described using the language "consisting essentially of" or "consisting of."

For purposes of better understanding the present teachings and in no way limit the scope of the teachings, it will be clear to one of skill in the art that the use of the singular includes the plural unless specifically stated otherwise. Therefore, the terms "a," "an" and "at least one" are used interchangeably in this application.

Unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. In some instances, "about" can be understood to mean a given value.+−0.5%. Therefore, for example, about 100 nm, could mean 95-105 nm. At the very least, each numerical parameter should at least be construed in light of the number of reported significant digits and by applying ordinary rounding techniques.

Various embodiments relate to antimicrobial functions for lighting systems and components. Various embodiments relate to a lighting method and system with blended antimicrobial additives transferred onto micro-structured patterned surfaces for the purpose of reducing bacterial growth and maintaining a sanitary environment, for example, in a healthcare facility.

Other embodiments provide lighting devices with effective antimicrobial activity in order to reduce the growth of bacteria, without increasing the antimicrobial levels, according to EPA and FDA restrictions. In various embodiments, the system and method provides a lighting system that decreases bio-adhesion between microbes and substrates, but also provides optical veiling and diffusing effect to meet lighting distribution requirements. Various embodiments also provide an environmental cleaning and antimicrobial lighting method and device that reduce the need for frequent cleaning requirements.

Still other embodiments provide a lighting system including lights, such as LED lights used, for example, in hospital LED lighting. The lighting system includes components, such as a diffuser, made from antimicrobial material comprising a micro-structured surface pattern. The surface pattern is configured to diffuse light to create the required light distribution, such as Lambertian and Bat-wing etc. With the surface exhibiting a Lambertian distribution, for example, all incident light is scattered from the light source with the radiance being the same for all directions. Thus, the light falling is scattered such that the apparent brightness to an observer is the same regardless of the observer's angle of view.

In addition, due to the pattern configuration, the micro-structured surface pattern also is capable of controlling bacterial migration, which extends the time required for cleaning maintenance. Micro-surface structures having a feature size greater than 500 nm will inhibit bacterial growth and increase the difficulty for microbes to adhere to surfaces. Thus, the micro-structured surface topography can also resist bio-adhesion of organisms and has anti-fouling effect.

An example of a lighting component configured according to the present teachings is a light diffuser produced with antimicrobial (AM) blended with plastic such as polymethlmethacrylate (PMMA) as a base article. On the base, a micro-structured pattern is applied as a top surface through a transfer molding process.

Figure 1:
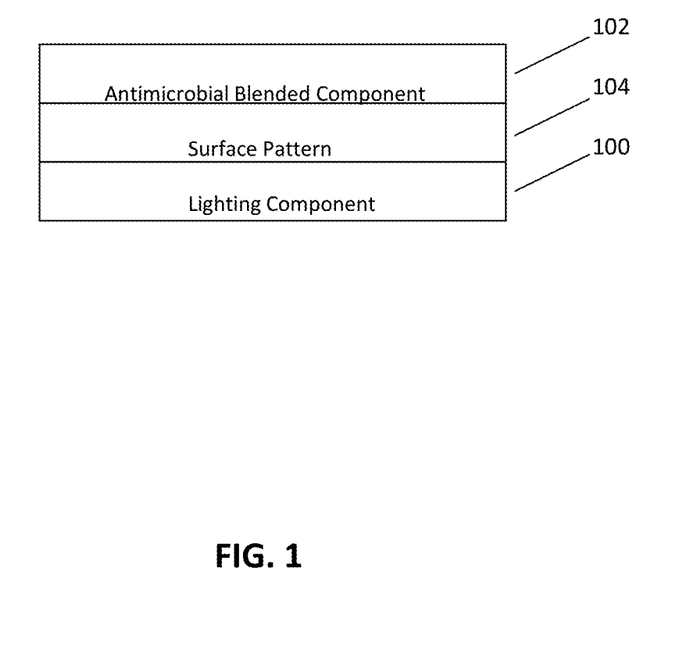
FIG. 1 is an illustration of an exemplary antimicrobial coating for products in accordance with embodiments of the present invention.

As shown in an example in FIG. 1, outer components, such as paints, plastics and coatings, in a lighting component 100, can be blended with antimicrobial additives to produce an antimicrobial blended component 102. The antimicrobial blended component 102 can be applied, as a coating, to exposed surfaces of the lighting component 100. These exposed surfaces often include patterns, such as a surface pattern 104.

In conventional systems, the exposed surfaces come into contact with microbes within the surrounding environment. In the absence of an antimicrobial blended protective component, these microbes pose a risk for bacteria growth. Therefore, the embodiments provide such outer components with antimicrobial properties so as to reduce the growth of bacteria and decrease bio-adhesion.

It should be understood that the term "antimicrobial additive" as used throughout the application means any chemical additive that reduces the level of bacteria, molds, fungi and other microbes and are commonly practiced as additives directly into plastic materials, coatings and paints etc. In various embodiments, one or more suitable antimicrobial additives can be selected from the following group: Ag, zinc and copper etc. ions doped carriers like zeolite, glass and some types of organic hosts, silver nano particles, tricolsan, and quaternary ammonium component etc. This list is merely exemplary and is not exclusive.

An "antimicrobial coating", as used herein, refers to any coating or paint or surface grown layer that includes an antimicrobial function for application to the surface of a device or component. The antimicrobial function can be from the additives above mentioned inside or can be a coating itself, such as titanium dioxide (TiO2) etc.

An "antimicrobial agent", as used herein, refers to a chemical that is capable of decreasing or eliminating or inhibiting the growth of microbes such a known in the art. The chemicals can be antimicrobial additive blended, antimicrobial additive alone, or precursors. The antimicrobial function begins after further reactions and processes, such as crosslinking, crystallizing, and polymerization etc.

Blended antimicrobial additives can be applied in different ways. One approach includes mixing an antimicrobial additive with a plastic, or some other substance. Parts are then formed by molding to produce a micro-structured surface pattern from molding process.

A second approach includes blending the antimicrobial additive into substance and then forming the micro-structured surface pattern via a secondary process such as etching, transfer molding, or thermal forming etc.

A third approach includes applying antimicrobial coatings to a regular substance. In this third approach, a micro-structured surface pattern can be formed during the coating process itself, using techniques such as roll to roll, and printing. The micro-structured surface pattern can also be formed after crystallization or polymerization, via a process such as transfer molding and thermal forming etc.

Yet another approach includes the initial step of forming the micro-structured surface pattern, as noted above. In this approach, an antimicrobial coating can be applied over the surface pattern afterwards. Those skilled in the art would recognize a variety of techniques that may be used to apply this layer to the lighting components, all of which would be within the spirit and scope of the present invention.

Figure 2:
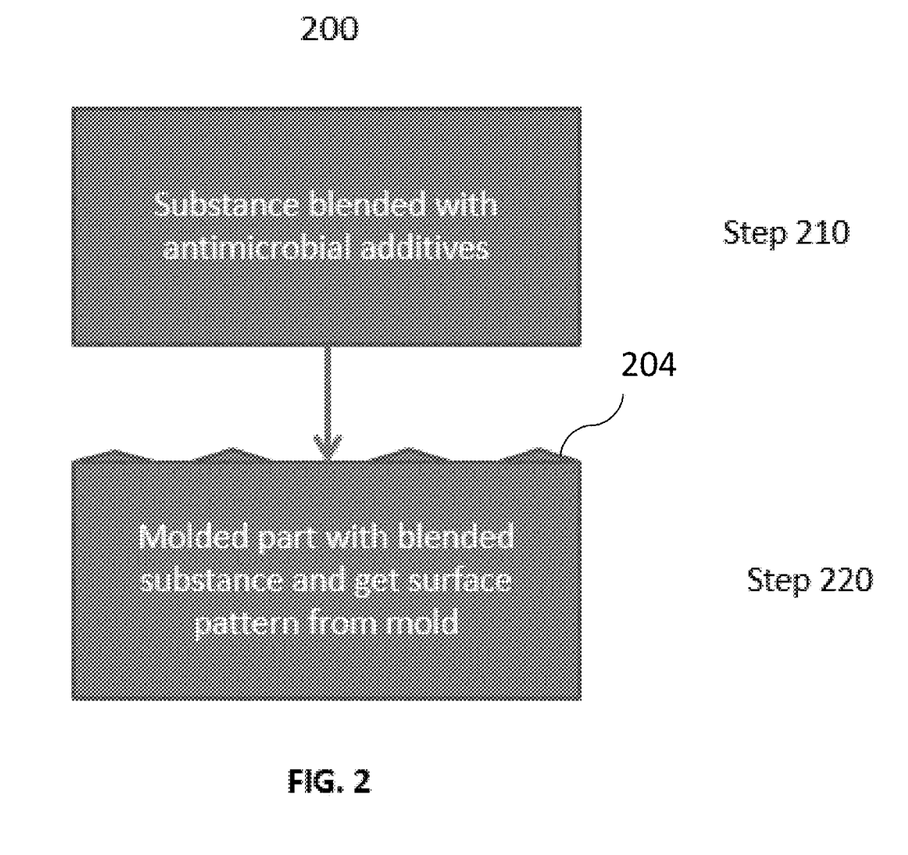
FIG. 2 is a flowchart of an exemplary method of practicing an embodiment of the present invention.
Figure 3:
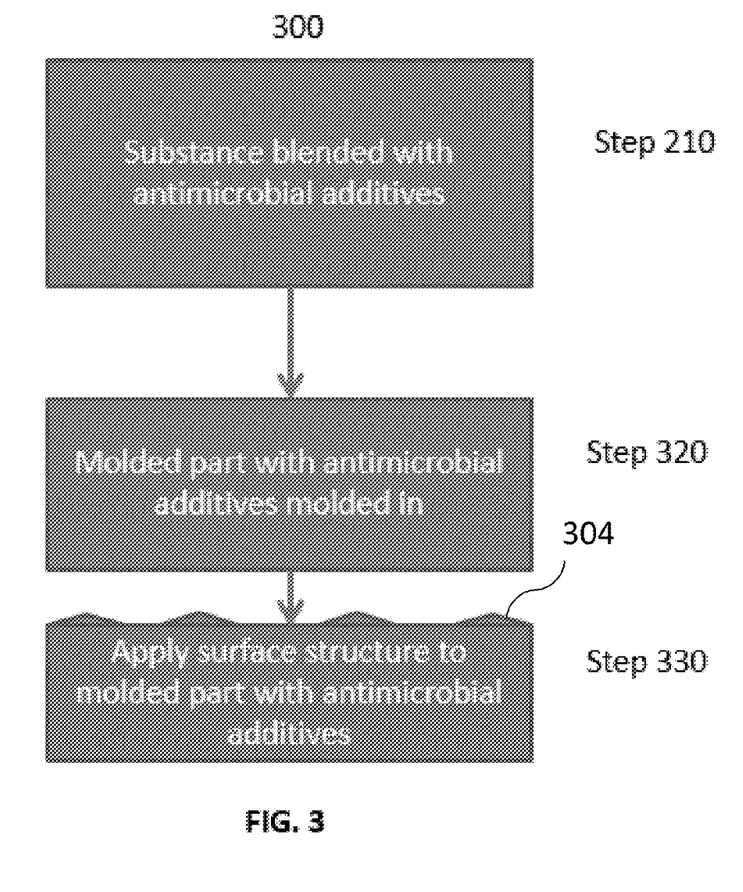
FIG. 3 is a flowchart of an exemplary method of practicing a second embodiment of the present invention.

The micro-structured surface pattern can be configured as either symmetric (depicted as 204, and 304 in FIGS. 2 and 3 or asymmetric (depicted as 404 in FIG. 4), depending on the lighting distribution requirements and appearance. Namely, the surface patterns can be applied uniformly, non-uniformly, (i.e., discontinuous) or geometrically, in particular in the form of symmetrical or asymmetrical patterns, distributed in a random or ordered way on the surface of the blended antimicrobial component. Regardless of the configuration of the surface patterns, this layer provides a functional pattern so as to provide the benefit of decreasing bio-adhesion between microbes and the substrate and preventing the growth of microbes.

In various embodiments, the micro-structured surface pattern can be configured such that the feature size and the space between adjacent features can vary from 100 nm to 100 µm. Due to the pattern configuration, the micro-structured surface pattern is capable of controlling bacterial migration, which extends the time required for cleaning maintenance. Micro-surface structures having a feature size greater than 500 nm will inhibit bacterial growth and increase the difficulty for microbes to adhere to surfaces even in dark environments. Thus, the micro-surface structured topography can also resist bio-adhesion of organisms and has anti-fouling effect.

Exhibiting the anti-fouling property, the micro-structured surface pattern protects the lighting components against microbial attachment and infestation. It is at the settling stage of fouling microbes that the adhesion and growth must be prevented. Because once settled and firmly attached, growth can be extremely rapid. The antimicrobial agent may become less effective and, sometimes, the microbes can only be removed by scrubbing and scraping. Thus, the anti-fouling property of the micro-structured surface pattern serves to prevent the microbes from settling onto substrates of the device.

By way of example, the lighting system can incorporate a lighting diffuser, as the lighting component shown in FIG. 1. The diffuser adjusts the light of the lighting system to an evenly distributed appearance. In an exemplary embodiment if the surface of the diffuser is asymmetric, the antimicrobial additive may need to include additional scatters like antimicrobial powders or $TiO_2$, etc. to minimize the light interference effects. For example, in an asymmetric embodiment, the micro-sized surface pattern shape can have an aspect ratio greater than 5:1. The aspect ratio is the ratio of the width of the shape to its height.

Any diffuser structure that provides homogenization and distribution of light can be utilized according to the present teachings. The diffuser precisely shapes, controls and distributes light, smoothing and homogenizing the illumination from a single or multiple LEDs. Examples of the diffuser, which can be utilized according to the present teachings, include volume diffusers.

The diffuser can be configured so that the light distribution can be controlled to meet the needs of a particular task or application. As an example, the diffuser can be configured to produce a long narrow illumination for lighting a hallway. In another example, the diffuser can be configured to redistribute the light into a uniform circular beam to illuminate a table or an operating table.

Diffusers can be specified by the full width at half maximum (FWHM) angle. The FWHM is the angle of diffusion that a collimated light becomes after passing through the diffuser. In this example, the FWHM of the light exiting the base volume diffuser may be configured to be greater than or equal to 20 degrees.

In various embodiments, the micro-structured surface pattern of the lighting system diffuses light to create a Lambertian light intensity distribution, as well as control bacterial migration.

Various embodiments provide a lighting system that decreases bio-adhesion between microbes and substrates, but also provides optical veiling and diffusing effect to meet light distribution requirements. An important aspect of a lighting system design is to control glare. Light sources produce several kinds of glare. One kind of glare is veiling glare, which is due to specular reflection from glossy surfaces. The image of the light source overlays the image on the glossy surface reducing contrast and, therefore, visibility. Veiling glare can be reduced by controlling the light beam from the light fixture to eliminate illuminating angles that would produce veiling glare in various applications.

One approach to reducing veiling glare is to place a diffuser in front of the light source. This lowers the surface luminance of the light fixture, but also reduces the loss of directional control of the light, which can result in veiling glare. Thus, the present invention is capable of preventing bio-adhesion and providing optical veiling and diffusing effects to meet the light distribution requirements.

In various embodiments, the antimicrobial additive particle size is desirably smaller than the finest feature size of micro-structure pattern. In this example embodiment, the requirement that the particle size could be smaller than the feature size serves. With the antimicrobial additive particle size smaller than the surface pattern feature size, the additive particle will reside inside the features and exit the surface pattern feature when microbes make contact with the surfaces and achieve an AM function.

FIGS. 2-5 are flowcharts of different exemplary methods of practicing embodiments of the present invention. The methods 200, 300, 400, and 500 provide a lighting system with enhanced antimicrobial properties, bio-adhesion resistance, and the ability to extend the required maintenance period for lighting fixtures is described herein. The method 200 includes a step 210.

In step 210, substances such as paints, plastics, and coatings are blended with antimicrobial additives. In Step 220 of the exemplary method, a micro-structured surface pattern 204 having, for example, a feature size and space between adjacent features varying between 100 nm to 100 μm can be obtained in the same molding process as the part is formed in the mold.

FIG. 3 depicts a method 300, similar to the method 200 and including the step 210. In a step 320, the component can be molded with the substance that is already blended with antimicrobial additives. In step 330, the molded component experiences a secondary process to obtain its micro-structured surface pattern 304 or structure. This secondary process can include, for example, etching, transfer molding and thermal forming etc.

Figure 4:
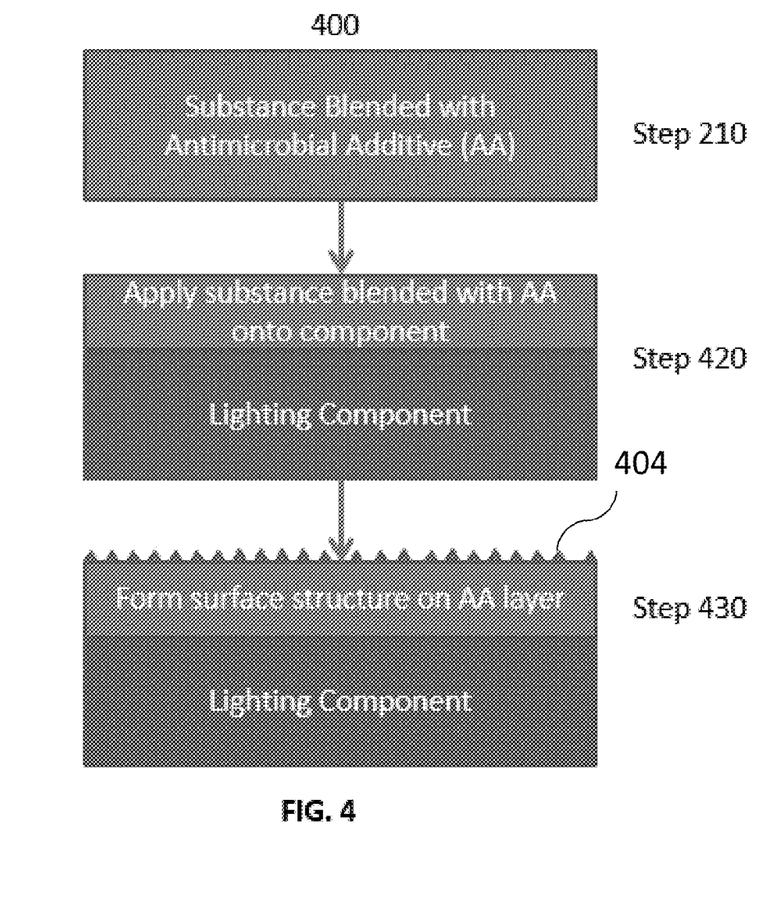
FIG. 4 is a flowchart of an exemplary method of practicing a third embodiment of the present invention.

FIG. 4 depicts a method 400, also similar to the method 200 and including the step 210. In step 420, after antimicrobial additives are blended into a substance, this blend is applied to the surface of the lighting component. In step 430, the micro-structured surface pattern 404 is then formed by one of the known processes noted above.

Figure 5:
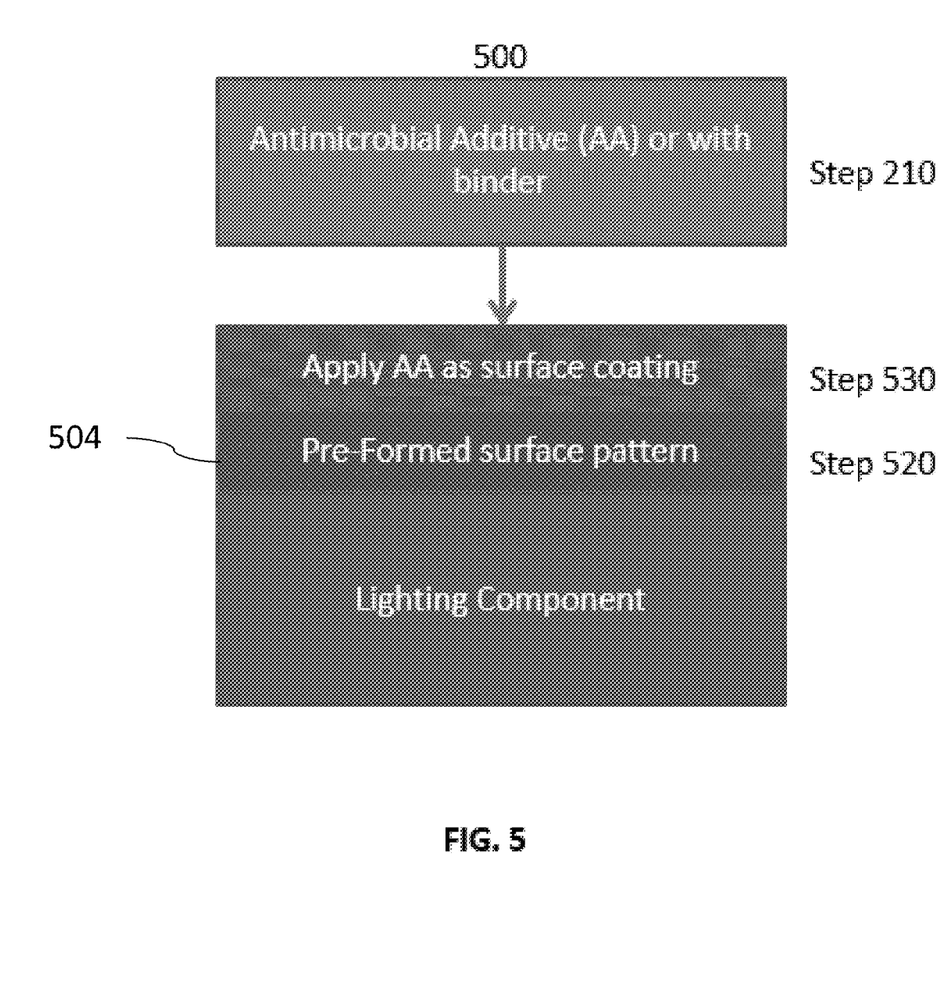
FIG. 5 is a flowchart of an exemplary method of practicing a fourth embodiment of the present invention.

FIG. 5 depicts a method 500, also similar to the method 200 and including the step 210. In step 520, the micro-structured surface pattern 504 is first formed on the lighting component via at least one of the known processes noted above. The substance blended with antimicrobial additives is then applied over the lighting component outer surfaces as a coating, depicted in step 530.

Generally, the embodiments provide techniques that enhance the antimicrobial function of traditional antimicrobial additives. For example, embodiments enhance antimicrobial doped plastics, paints, and coatings. The enhancements are achieved through the micro-structured surface pattern being a design of various geometric characteristics such as structure size, shape and space, etc. Techniques constructed in accordance with the embodiments not only decrease the bio-adhesion between microbes and substrates, but provide optical veiling and diffusing effect to meet light distribution requirements.

Without adding additional antimicrobial additives, which are restricted and regulated by the EPA and the FDA, the lighting system and method enhance the control of bacterial growth by combining the antimicrobial additives and micro-structured surface pattern on outer surfaces of a lighting fixture. This can physically decrease bio-adhesion between microbes and substrates. The system and method combine a surface micro-structured feature onto an antimicrobial component to create a single component.

Testing was conducted for an AgION and Ag glass antimicrobial additive doped plastics and micro-pattern surface diffusers prepared according to the embodiments regarding the proliferation of microbes and the viability of the microbes. The proliferation and the viability of the microbes were tested with the JIS Z 2801 test method. The JIS Z 2801 test method is designed to quantitatively test the ability of plastics and other antimicrobial surfaces to inhibit the growth of microorganisms or kill them over a 24 hour period of contact.

The test results showed continuous inhibition of microbe growth. These experiments were repeated several times with the same results. Thus, it is clearly evident that the components prepared according to the embodiments are effective antimicrobial agents.

Alternative embodiments, examples, and modifications which would still be encompassed by the invention may be made by those skilled in the art, particularly in light of the foregoing teachings. Further, it should be understood that the terminology used to describe the invention is intended to be in the nature of words of description rather than of limitation.

Those skilled in the art will also appreciate that various adaptations and modifications of the preferred and alternative embodiments described above can be configured without departing from the scope and spirit of the invention.

Therefore, it is to be understood that, within the scope of the appended claims, the invention may be practiced other than as specifically described herein.

We claim:

1. A lighting system comprising:
   a light fixture including a light diffuser;
   the light diffuser configured to be exposed to air, and comprising a micro-structured surface pattern at an outer surface thereof; and
   a blended layer comprising an antimicrobial additive in the form of a coating as a separate layer applied to the micro-structured surface pattern of the light diffuser,
   wherein the blended layer together with the micro-structured surface pattern on the outer surface of the light diffuser are configured to perform optical veiling and diffusing light while controlling growth of microbes onto the light diffuser of the light fixture.

2. The system according to claim 1, wherein the antimicrobial additive combined with the outer component by at least one of blending and coating onto an outer surface of the outer component of the light fixture; and wherein the outer surface is selected from the group consisting of paints, plastic, and coatings.

3. The system according to claim 1, wherein the antimicrobial additive includes at least one of zeolite and glass with silver (Ag), copper or zinc ion, tricolsan, and a quaternary component.

4. The system according to claim 1, wherein the micro-structured surface pattern is further configured to control bio-adhesion between the microbes and the light diffuser of the light fixture.

5. The system according to claim 4, wherein the micro-structured surface pattern is a symmetric pattern.

6. The system according to claim 4, wherein the micro-structured surface pattern is an asymmetric pattern.

7. The system according to claim 4, wherein the micro-structured surface pattern has a feature size and space between adjacent features in the range of approximately 100 nm to approximately 100 μm.

8. A method of use of a lighting system, comprising:
   providing a light diffuser of a light fixture configured to be exposed to air;
   forming a micro-structured surface pattern on an outer surface of the light diffuser;
   applying a blended layer comprising an antimicrobial additive as a separate layer in the form of a coating to the micro-structured surface pattern of the light diffuser; and
   performing optical veiling and diffusing light using the blended layer and the micro-structured surface pattern while controlling, by the micro-structured surface pattern and the blended layer, growth of microbes onto the light diffuser of the light fixture.

9. The method according to claim 8, wherein the outer surface of the light diffuser is selected from the group consisting of paints, plastic, and coatings.

10. The method according to claim 8, wherein the antimicrobial additive comprises at least one of carriers including zeolite and glass with silver (Ag), copper or zinc ion, tricolsan, and a quaternary component.

11. The method according to claim 8, further comprising controlling, by the micro-structured surface pattern bio-adhesion between the microbes and the light diffuser of the light fixture.

12. The method according to claim 11, wherein the micro-structured surface pattern is a symmetric pattern.

13. The method according to claim 11, wherein the micro-structured surface pattern is an asymmetric pattern.

14. The method according to claim 8, further comprising forming the micro-structured surface pattern with the lighting fixture.

15. The method according to claim 8, further comprising:
   applying the blended layer to the outer component; and
   forming the micro-structured surface on the blended layer.

16. The method according to claim 14, further comprising:
   forming the micro-structured surface pattern; and
   applying the blended layer on the micro-structured surface pattern.

17. The method according to claim 14, wherein the micro-structured surface pattern is formed by etching of or molding with a surface of the lighting fixture.

* * * * *